United States Patent [19]

Saferstein et al.

[11] Patent Number: 5,134,229
[45] Date of Patent: Jul. 28, 1992

[54] PROCESS FOR PREPARING A NEUTRALIZED OXIDIZED CELLULOSE PRODUCT AND ITS METHOD OF USE

[75] Inventors: Lowell Saferstein, Edison; Stephen Wolf, Neshanic Station; Lola Kamp, Highland Park; Cary Linsky, East Brunswick; David Wiseman, Highland Park, all of N.J.

[73] Assignee: Johnson & Johnson Medical, Inc., Arlington, Tex.

[21] Appl. No.: 624,452

[22] Filed: Dec. 13, 1990

Related U.S. Application Data

[63] Continuation-in-part of Ser. No. 464,060, Jan. 12, 1990, abandoned.

[51] Int. Cl.$^5$ ............ C08B 15/02; C08B 23/02; A61K 31/70
[52] U.S. Cl. ............ 536/56; 424/443; 424/444; 424/446; 424/447; 536/124; 604/292; 606/213; 602/900
[58] Field of Search ............ 424/443, 444, 446, 447; 604/292; 606/213; 536/56, 124; 128/156, 325

[56] References Cited

U.S. PATENT DOCUMENTS

| | | | |
|---|---|---|---|
| 3,666,750 | 5/1972 | Briskin et al. | 536/56 |
| 4,277,463 | 7/1981 | Tomic | 424/679 |
| 4,329,383 | 5/1982 | Joh | 536/21 |
| 4,415,490 | 11/1983 | Joh | 536/21 |
| 4,597,960 | 7/1986 | Cohen | 424/447 |

FOREIGN PATENT DOCUMENTS 1593513 7/1981 United Kingdom.

OTHER PUBLICATIONS

E. S. Hurwitt et al., American Journal of Surgery, vol. 100, Sep. 1960, pp. 439–446.
Chem. Abs., vol. 75, 1971, 4037g.
Dol'berg, E. B., Oridoroga, V. A.; Shuteeva, L. N. Yasnitskii, B. G., *Farm. Zh.* (Kiev) 1971, 26(2), 5306 (Ukrain).

*Primary Examiner*—Ronald W. Griffin

[57] ABSTRACT

Oxidized cellulose material is neutralized, by contacting an acidic oxidized cellulose material with a water and alcohol solution of a basic salt of a weak organic acid, e.g. sodium acetate, to elevate the pH of the cellulosic material to between 5 and 8. The resulting neutralized product is storage stable and has therapeutic applications, including hemostasis and adhesion prevention. Furthermore, the neutralized product may be impregnated with acid-sensitive hemostatic agents, such as thrombin, to enhance its hemostatic properties, or with acid-sensitive adhesion-preventive agents, such as t-PA, to enhace its adhesion-prevention properties.

22 Claims, No Drawings

PROCESS FOR PREPARING A NEUTRALIZED OXIDIZED CELLULOSE PRODUCT AND ITS METHOD OF USE

CROSS-REFERENCE TO PRIOR APPLICATION

This is a continuation-in-part application of U.S. application Ser. No. 464,060, filed Jan. 12, 1990 now abandoned.

FIELD OF THE INVENTION

This invention relates to a process for preparing a storage stable oxidized cellulose product and its method of use. More particularly, the invention relates to a process for preparing a storage stable product comprising a neutralized oxidized cellulose material which may also include acid-sensitive medicaments, biologics, enzymes, and adhesion-preventive substances. Neutralized oxidized cellulose cloth may be applied to a hemorrhaging site of a mammal for hemostasis, or it may be positioned between a site of surgical activity and neighboring tissue to prevent post operative adhesions.

BACKGROUND OF THE INVENTION

Doub et al. in U.S. Pat. No. 2,517,772 describes the impregnation of neutralized oxidized cellulose products with thrombin. Doub et al. discloses a method of neutralizing oxidized cellulose cloth with an aqueous sodium bicarbonate solution (Example 2) or an aqueous calcium acetate solution (Example 1). Example 2 of the Doub et al. patent discloses neutralizing oxidized cellulose gauze with an aqueous solution of strongly basic sodium bicarbonate and then impregnating the neutralized product with thrombin. The thrombin impregnated gauze is then frozen and dried from the frozen state to allegedly provide a highly hemostatic surgical dressing.

The present inventors have found that utilization of aqueous solutions of sodium bicarbonate to neutralize oxidized cellulose cloth results in a cloth that is partially gelled, distorted from its original size and very weak with little integrity. The tensile strength of the cloth is too low for practical use such as, for example, a hemostat.

Study of oxidized cellulose cloth that has been neutralized with calcium acetate in accordance with the teachings of Example 1 of the Doub et al. patent provided a cloth that is of acceptable integrity but is irritating to mammalian skin and other body cells at point of contact. Further, large, whitish masses presumed to be granuloma tissue formed at the application site of the cloth. Apparently, such tissue is attempting to encapsulate the calcium salt of the oxidized cellulose cloth. The patent to Doub et al. does not disclose any practical data pertaining to testing in animals.

The present inventors have found that the use of strongly basic aqueous sodium hydroxide, ammonium hydroxide, and sodium carbonate solutions to neutralize oxidized cellulose cloth all lead to considerable shrinkage and loss of tensile strength to the cloth. The use of dry ammonia gas produces a pronounced browning of the cloth and rapid gelation of the cloth when it is wetted thus making it impractical for use as a therapeutic product such as a surgical dressing.

Barinka et al. in British Pat. 1,593,513 disclose a process for oxidizing cellulose with a mixture of nitric acid and stabilized ("phlegmatized") sodium nitrite. The material is then stabilized with an aqueous-alcoholic solution of urea or its N,N-disubstituted alkyl or acyl derivatives. Finally, the oxidized cellulose is converted to its calcium, sodium, or ammonium salt by repeatedly alternating absorption-in and centrifuging-off a solution of an equimolar mixture of chloride and acetate of calcium, sodium or ammonium.

Oxidized cellulose fabrics are bioresorbable and absorbent matrices capable of convenient application to tissue surfaces. Two examples of such a fabric are INTERCEED* (TC7) Absorbable Adhesion Barrier and SURGICEL* Absorbable Hemostat. However these materials are acidic. The PH of the aqueous phase of 1 g of INTERCEED Barrier suspended in 100 ml of purified water is approximately 4.1. The surface PH of a fully water-saturated piece of fabric is about 1.7. Materials such as thrombin, tissue plasminogen activator analogue (t-PAA), and other highly acid-sensitive materials are inactivated immediately on such a matrix, Precluding their use for delivery to the site of implantation at the time of surgery. At this pH an active agent such as heparin does not lose its activity immediately, thus allowing delivery at the time of, or shortly before surgery, but will be inactivated over time. This precludes the use of INTERCEED Barrier impregnated with heparin as a patient ready storage-stable product.

It is therefore an object of the present invention to provide a storage stable neutralized oxidized cellulose cloth with a PH of from 5 to 8, which retains its integrity and tensile strength for practical use and therapeutic application and can advantageously be impregnated with acid-sensitive medicaments, biologics, enzymes, and adhesion-preventive substances.

SUMMARY OF THE INVENTION

The foregoing object of providing a strong, practical, convenient-to-use and storage-stable oxidized cellulose cloth has now been accomplished in accordance with the processes and methods of the present invention.

In accordance with the purposes of the invention, as embodied and fully described herein, the invention comprises a process for preparing a storage stable non-irritating and therapeutic neutralized oxidized cellulose product comprising the steps of: contacting an acidic oxidized cellulose material with a water and alcohol solution of a slightly basic salt of a weak acid to elevate the pH of the cellulose material to between 5 and 8; washing this material with alcohol to remove any excess salt and water; and drying the cellulosic material to remove alcohol. (In this specification and the appended claims, unless a different method is specified, pH is determined of the aqueous phase of 1 g of the material in 100 ml of freshly boiled purified water.)

In further embodiments, the cellulosic material is air-dried and impregnated with an effective amount of an acid-sensitive medicament, biologic or enzyme. For hemostasis, the medicament is preferably thrombin. For prevention of post surgical adhesions, the medicament is an adhesion-preventive substance, such as tissue plasminogen activator (t-PA), tissue plasminogen activator analogue (t-PAA), streptokinase, heparin, low molecular weight heparin, or pentasaccharide.

In preferred embodiments the slightly basic salt of a weak acid is a chloride-free organic acid salt selected from the group consisting of sodium acetate, potassium acetate, sodium citrate, sodium formate, potassium citrate, potassium formate, and mixtures thereof. In other preferred embodiments the slightly basic salt of a weak acid is a chloride-free inorganic acid salt such as disodium hydrogen phosphate, dipotassium hydrogen phosphate, or mixtures thereof.

In preferred embodiments of the process of the invention the water and alcohol solution has a ratio of about 3:2 to about 1:1 of alcohol to water. preferably the alcohol used is methanol. The invention is also directed to storage stable neutralized oxidized cellulose products produced by the process of the invention which may or may not be impregnated wlith an effective amount of acid-sensitive medicament.

As embodied and described herein the invention also comprises the products produced by the process of the invention.

As embodied and described herein the invention further comprises a mammalian hemostatic method comprising the step of applying to a hemorrhaging site of a mammal the neutralized oxidized cellulose cloth product produced by the process of the invention, having pH in the range between about 5 and 8, and optionally impregnated with thrombin.

The invention further comprises a process for preventing surgical adhesions, which comprises positioning as a physical barrier, between the site of the surgical activity and neighboring tissue, a neutralized oxidized cellulose material produced by the process of the invention, having pH in the range between about 5 and 8, and optionally impregnated with a surgical adhesion-preventive substance.

DETAILED DESCRIPTION OF THE PREFERRED EMBODIMENTS OF THE INVENTION

Reference will now be made in detail to preferred embodiments of the invention, examples of which are illustrated in the following examples section.

In accordance with the process of the invention the oxidized cellulose material is neutralized to a pH of between 5 and 8. The cellulose material may be a substrate such as a cloth, sponge, paper or film. For convenience this is referred to as cloth in subsequent references but it is understood by this term that any suitable material could be used. In this pH range, acid-sensitive therapeutic materials including medicaments, biologics and enzymes can be applied to the cloth and remain viable and therapeutically effective. Further, the neutralization process of the invention unexpectedly produces a cellulosic material which retains its integrity and tensile strength while minimizing shrinkage which enables it to be practically used, for example, by surgeons as a surgical dressing or hemostat.

In preferred embodiments of the invention the neutralized cloth can be used as a surgical dressing to cover a wound to keep it clean and moist. In other embodiments the cloth is impregnated with medicaments such as, for example, growth factors, bactericidal agents, or antihistamines. Such agents slowly leach out of the cloth and into the wound bed to assist the wound in healing faster. This cloth when neutralized and impregnated with medicaments, provides a bioabsorbable wound covering with good therapeutic value.

The neutralization of oxidized cellulose cloth is accomplished with mild neutralizing agents such as the sodium or potassium salts of weak acids, for example sodium acetate, in water or a mixture of water and alcohol. The neutralized oxidized cellulose product produced by this process provides a strong (i.e. good tensile strength and integrity), convenient-to-use, storage-stable, and hemostatically effective cloth composition. This is in contrast with attempted use of stronger bases such as sodium hydroxide, ammonium hydroxide, sodium carbonate or sodium bicarbonate which undesirably cause the neutralized cloth to unacceptably weaken and partially gel. Furthermore, the oxidized cellulose is neutralized without chloride to avoid forming hydochloric acid which is a by-product of the reaction of chloride with the oxidized cellulose. Strong acids such as hydrochloric acid can cause oxidized cellulose to decompose into low molecular weight polymer, with loss of tensile strength and shortened shelf life. Weak acid does substantially no damage to the oxidized cellulose cloth.

The neutralization reaction can be carried out in water or alcohol alone but is preferably carried out in mixtures of water and alcohols. The use of a mixture of water and alcohol provides good solubility for the weak acid salts via the water, and the alcohol prevents the oxidized cellulose from excessively swelling, distorting and weakening during the neutralization. Thus the physical properties of the material are retained. Methanol is the preferred alcohol because many of the above-mentioned salts have good solubility in this alcohol in combination with water. Preferably, the alcohol to water ratio has a range of about 4:1 to 1:4 . If the solution becomes too rich in alcohol, some salts may no longer be soluble particularly if the alcohol is other than methanol. If the solution becomes too rich in water, some swelling of the cloth will occur as neutralization takes place and there will be some loss in physical properties such as in the tensile strength of the cloth. Other useful alcohols include, for example, ethyl alcohol, propyl alcohol and isopropyl alcohol.

The use of a mild neutralizing agent such as sodium acetate allows for control of the degree of neutralization. Use of stoichiometric and chemically equivalent amounts of neutralizing agent and carboxylic acid on the oxidized cellulose cloth does not produce a 100% neutralized cloth as would be produced with strong irreversible reactions with bases such as sodium hydroxide, sodium carbonate, sodium bicarbonate and ammonium hydroxide.

Oxidized cellulose behaves as an ion exchanger and will pull out of solution the metal cation of any salt that is passed over it. The by-product of this exchange is an acid from the salt and by using a salt of a weak organic acid, a weak acid such as acetic acid is produced which does no damage to the cloth. Using salts of strong acids such as sodium chloride or sodium sulfate produces hydrochloric acid or sulfuric acid by-products respectively, and these strong acids can cause damage such as depolymerization of the cloth.

When using sodium or potassium salts of weak acids, the sodium or potassium ion is exchanged for a proton on the oxidized cellulose and part of the salt is converted to weak acid. The mixture of acid and salt in the solution results in a buffered solution which maintains a fairly constant pH and controls the degree of neutralization. An equilibrium reaction is established whereby the sodium or potassium ions are bound to the acid portion of the oxidized cellulose cloth and also to the salt molecules. This partitioning of the sodium or potassium ions prevents the neutralization of the cloth from going to completion which would result in a very weak and swollen cloth when wetted with water.

For example, disodium hydrogen phosphate ($Na_2HPO_y$) is a weak base and when a solution of this salt is passed through oxidized cellulose, the cloth pulls out one sodium ion and forms the sodium salt of oxidized cellulose and a weak acid dihydrogen sodium phosphate ($H_2NaPO_4$). The formation of dihydrogen sodium phosphate in the presence of disodium hydrogen phosphate forms a desirable buffer which keeps the pH of the solution sufficiently constant during the neutralization reaction.

Using a stoichiometric amount of, for example, sodium acetate brings about a 65-75% degree of neutralization of the carboxylic acid groups on the oxidized cellulose polymer. This control of pH by creating a self generating buffered solution and the use of methanol to control the swelling of the cloth, leads to a sufficiently neutralized cloth so that acid-sensitive medicaments such as thrombin, acid-sensitive biologics or enzymes, and acid sensitive adhesion-preventive substances may be added to it while at the same time the physical properties, e.g. tensile strength and shape of the cloth, are preserved.

The preferred process of preparing storage stable oxidized cellulose products in accordance with the invention comprises the steps of first contacting an acidic oxidized cellulose material (pH of about 4.1) with a water and alcohol solution of sodium acetate to elevate the pH of the cellulose material to between 5 and 8. The alcohol to water ratio is from 4:1 to 1:4, more preferably the alcohol solution is about a 3:2 to 1:1 mixture of methanol and water.

The amount of sodium acetate salt used depends upon the degree of neutralization desired for the cloth and may be less than, equal to or up to two times the molar equivalent of carboxylic acid content of the oxidized cellulose cloth. Most preferred is an amount of salt stoichiometric with the carboxylic acid content of the cloth. The following method is used to determine the amount of sodium acetate needed to neutralize 100 grams of oxidized cloth with a carboxylic acid content of 18 weight percent. The weight of the cloth (100 grams) is multiplied by the percent carboxylic acid to obtain the weight of the carboxylic acid portion; thus $100 \times 0.18 = 18$ grams of carboxylic acid. This is divided by the molecular weight of the carboxylic acid group (COOH), 45, to give the moles of carboxylic acid. Thus, $18/45 = 0.40$ moles. The moles of sodium acetate required to neutralize the oxidized cloth is stoichiometric with the moles of acid, or 0.40 moles of sodium acetate. The molecular weight of sodium acetate, 82, is multiplied by 0.40 to determine that 32.8 grams of sodium acetate are needed to neutralize the 100 grams of oxidized cellulose cloth.

The amount of sodium acetate used is generally about equal to or up to twice the stoichiometric amount of carboxylic acid content of the cloth. Alternatively, a second charge of a stoichiometric amount of sodium acetate can be used if the reaction is recharged with fresh solvent and salt after the first charge reaches a constant pH. The cellulosic material with elevated pH is then washed with alcohol to remove the excess water, sodium acetate salt and ions therefrom.

The method of neutralizing the oxidized cloth is also improved by using a pump to circulate the neutralizing agent through the cloth and by controlling the amount of neutralization by monitoring the pH of the circulating solution. An example of a pump used to circulate the solution of neutralizing agent around and through the oxidized cellulose cloth is a constant temperature bath with a built in pump for external circulation of solutions (e.g. Brookfield EX-100 brand bath pump). The pump circulates the solution of water/alcohol and neutralizing agent around the cloth which is wrapped around a core in a canister with an inlet leading up the center of the core and an outlet to return the neutralizing solution to the circulating bath. The type of pump utilized is not critical to this invention as other types of pumps may work just as well.

To carry out the neutralization a circulating bath with pump is filled with the alcohol and water, the neutralizing agent such as sodium acetate is added and the pump turned on. The progress of the neutralization is monitored by a pH probe which should reach a constant value when the neutralization is complete. At this time the reaction is over and the cloth is removed from the canister and washed with methyl alcohol by immersing it in a beaker containing sufficient alcohol to cover the cloth. The cloth is then air dried to remove any excess water and alcohol. At this point, the pH of the cloth is above 5.

The preferred alcohol to use for washing is again methanol although other alcohols such as ethyl alcohol, propyl alcohol, and isopropyl alcohol may be substituted for methanol so long as the neutralizing agent, e.g. sodium acetate is soluble in solution thereof.

The air-dried material may in certain preferred embodiments be impregnated with therapeutically effective amounts of acid-sensitive medicaments, biologics or enzymes, for example, a hemostatic effective amount of thrombin or, alternatively, an effective amount of an adhesion-preventive substance. Thrombin is a proteolytic enzyme which catalyzes the conversion of fibrinogen to fibrin which leads to the formation of blood clots.

For hemostasis, the cloth may also be impregnated with fibrinogen, which will assist in the formation of a strong clot when converted to fibrin by thrombin. Fibrinogen is a soluble plasma protein that is converted to the insoluble fibrin clot by the action of the enzyme thrombin. Fibrinogen is present in normal plasma at a concentration between 2-6 mg per ml, and is indispensable for blood coagulation. An exogenous source of fibrinogen produces a stronger and faster sealing of the wound. The neutralized cloth is dipped into a solution of fibrinogen and applied to the bleeding wound. The cloth is then sprayed with a thrombin solution which instantly causes the fibrinogen to form a fibrin clot and seals the wound shut. The neutralized cloth provides a scaffold of fibers to reinforce the clot, and make it stronger. The neutralized cloth being bioabsorbable will dissolve in 7-14 days. The cloth may also contain antifibrinolytics such as Aprotinin which prevent the blood clot from dissolving too quickly. This is particularly important in some surgical procedures, where premature clot dissolution will lead to rebleeding.

Thrombin cannot be applied to a substrate material that is too acidic, i.e. less than about pH 5, because it will rapidly be inactivated upon contact. In the case of the neutralized cloth hemostat of the invention, an aqueous solution of thrombin may be directly applied thereto and freeze-dried to provide a patient ready, storage stable hemostat. The neutralized cloth may be impregnated with thrombin at the time of surgery by wetting the cloth with a freshly prepared aqueous solution of thrombin and applying this to a bleeding site. The neutralized cloth permits this procedure to be carried out since no thrombin is inactivated.

It has also been found that neutralized oxidized cellulose cloth is a more effective hemostat than the starting material, i.e. non-neutralized (acidic) oxidized cellulose, the reason being that the acidic oxidized cellulose fabric (pH of about 4.1) deactivates the naturally occurring thrombin at the site of the wound until the buffering action of blood brings the pH of the cloth to about 5 which is in the stable range for thrombin. The neutralized cloth on the other hand is already in the stable pH range for thrombin and therefore acts as a hemostat much faster. Sodium neutralized cellulosic material has an unexpected increased hemostatic efficacy (on the order of about a 50% reduction in bleeding time) over non-neutralized cellulosic materials. The preferred amount of thrombin utilized per milligram of hemostatic material is from 3.5 to about 9 units of thrombin per milligram of fabric which results in 70%-85% of the thrombin remaining after more than 2 years when stored in an air tight vessel at refrigeration temperature. A unit of thrombin is a measure of the potency of the thrombin when it reacts with fibrinogen from the blood. A unit of thrombin is defined as the amount of thrombin needed to clot the fibrinogen in 1 ml of plasma in 15 seconds.

The thrombin-impregnated neutralized cellulosic material can effectively be used as a practical hemostat in surgical procedures on mammals. The storage-stable hemostat product should be kept refrigerated until it is ready for use, when it is applied directly to a hemorrhaging site or is wrapped around a blood vessel to produce hemostasis. The thrombin not only retains its viability and efficacy upon contact with the neutralized oxidized cellulose material but remains storage stable for long periods of time under refrigerated conditions, e.g. about 4° C. Thrombin applied in accordance with the process of the invention will retain up to 70-85% of its hemostatic activity for more than two years.

Neutralized oxidized cellulose cloth, optionally impregnated with an acid-sensitive adhesion preventive substance, is also useful in preventing formation of post operative adhesions, even at a bleeding surgical site. An example of such an acid-sensitive adhesion preventive substance is heparin, which prevents fibrin from forming at a surgical site and is thus useful in preventing surgical adhesions. A fibrinolytic enzyme such as t-PAA is similarly useful in prevention of surgical adhesion formation by lysing fibrin which is present at the surgical site.

Other examples of adhesion-preventive agents which might be sensitive to an acid delivery system by long or short term contact include other glycosaminoglycans (such as dermatan sulfate, heparan sulfate), other fibrinolytic enzymes such as t-PA, streptokinase, urokinase, and prourokinase, non-fibrinolytic enzymes, antibiotics, low molecular weight heparins, heparinoids, synthethic heparins, synthetic heparin fragments, pentasaccharide, calcium channel blockers, steroids, and thrombin inhibitors (such as thirudin) pentasaccharide may be particularly useful for adhesion prevention on a neutralized matrix as it has the unique property of achieving an antithrombotic effect without causing as much derangement in the blood dynamics as the heparins and other anticoagulant drugs. Thus, using the pentasaccharide, one would expect the prevention of adhesion-generating fibrin formation without the unnecessary risk of bleeding. (Science Focus, The New York Academy of Sciences, 1988, Vol. 2, No. 3; Walenga, J. M. et al., The inhibition of the generation of thrombin and the antithrombotic effect of a pentasaccharide with sole antifactor Xa activity, Thrombosis Research 51;21, 1988.)

Preparations of neutralized material are made covering the pH range from about 5 to 8 to deliver these agents, with neutralized oxidized celluloses having lower carboxyl content providing greater integrity upon neutralization to higher pH. The invention broadens the scope of the kinds of surgical adhesion-preventive substances capable of delivery to a surgical site on a matrix capable of maintaining it there by virtue of the absorbent, bioresorbable, and pH compatible properties of the matrix. It also permits the preparation of a dried patient-ready product impregnated with an active agent that is unstable at low pH.

Other acid-sensitive medicaments, enzymes and biologics that may be advantageously applied to the neutralized oxidized cellulose cloth for therapeutic use include antifibrinolytics that prevent a clot from dissolving too fast, such as Aprotinin or Trasylol*; growth factor compositions, such as platelet derived growth factors or epidermal derived growth factor to speed wound healing; and glycosaminoglycans, such as chondroitin sulfate and hyaluronic acid, which are biologics found useful in healing wounds.

EXAMPLES

The invention will now be illustrated by examples. The following examples represent preferred embodiments of the compositions, processes and methods of the invention. The examples are not intended to be limiting of the scope of the present invention but read in conjunction with the detailed and general description above provide further understanding of the present invention and an outline of a process for preparing the products of the invention and practicing the methods of the invention.

EXAMPLE 1

Preparation of Neutralized ORC Cloth in 3 parts Methyl Alcohol, 2 parts Water with Sodium Acetate as the Neutralizing Agent A quantity of 71.9 grams of oxidized regenerated cellulose (ORC) fabric with a carboxylic acid content of 15.2% was wrapped around a perforated core and placed in a reactor equipped with a circulating pump. The reactor was filled with a mixture of 3 liters of water and 2 liters of methyl alcohol. A Brookfield EX-100 constant temperature bath with built-in pump for external circulation of solutions was turned on to pump the solvent through the center of the perforated core and through the plies of cloth wrapped around the core. The solvent flowed through the exit line and recirculated again through the pump and back to the core.

A stoichiometric amount of sodium acetate trihydrate equal to the number of moles of carboxylic acid on the cloth was added to the solution; i.e., $71.9 \times 15.2\% = 10.92$ grams of carboxylic acid; $10.92/45 = 0.242$ moles of carboxylic acid; $0.242 \times 136.1 = 33.05$ grams of sodium acetate trihydrate.

The 33.05 grams of sodium acetate trihydrate were added to the aqueous alcohol solution and circulated by pump around and through the fabric for 30 minutes. After 30 minutes the pH of the circulating solution reached a constant value (pH 4.6). The cloth was being neutralized with a buffer solution consisting of a mixture of sodium acetate and acetic acid which is a by-product from the reaction of sodium acetate with the oxidized cellulose. It is this self-generating buffer that allows the oxidized cellulose cloth to be neutralized without loss of physical properties.

At this point the neutralization was complete, and the fabric was removed from the reactor and placed in 600 ml of methanol for 10 minutes. After 10 minutes, the alcohol was removed and replaced with another 600 ml of fresh methanol. The methanol washed the water and any excess sodium acetate from the cloth. After the second wash, the cloth was hung up and air dried. The pH of the cloth was measured by placing 1 gram of cloth in 100 ml of purified water and stirring rapidly in a blender for 1 minute. The solution was filtered away from the shredded cloth and the pH of the filtrate was measured. The pH was 6.5, as compared with 3.3 for the original unneutralized cloth. When this cloth was titrated with standard sodium hydroxide for carboxylic acid content, it was found to be 5.32% by weight carboxylic acid. The original unneutralized cloth had a carboxylic acid content of 15.2%, indicating that 65% of the carboxylic acid groups had been neutralized: $(15.2-5.32)/15.2 \times 100 = 65\%$.

pH measurements of batches of INTERCEED* Barrier and neutralized (N-INTERCEED) Barrier were compiled as follows:

| pH of One Gram of Test Material in 100 ml of Freshly Boiled Purified Water | | | |
|---|---|---|---|
| Test Material | Number of Batches | pH Range | Median pH |
| INTERCEED | 11 | 3.9–4.3 | 4.1 |
| N-INTERCEED | 8 | 5.3–7.2 | 6.7 |

Determinations also were made of the surface pH of representative batches of each material by saturating a 3"×4" piece of the fabric with 2 ml of freshly boiled purified water and measuring the pH with a surface electrode. The relevance of this test is to closely approximate the actual pH experience of an acid-sensitive medicament on the surface of the matrix.

| pH Determination of Saturated Fabric by Surface Electrode | | | |
|---|---|---|---|
| Test Material | Number of Batches | pH Range | Median pH |
| INTERCEED | 6 | 1.64–1.93 | 1.72 |
| N-INTERCEED | 2 | 4.20–4.48 | 4.34 (avg.) |

The neutralized cloth is white, strong, can be sterilized by cobalt irradation, and is stable for several years when packaged dry. When implanted subcutaneously into a rat, the neutralized cloth absorbs within the same time period as unneutralized cloth. This cloth is also sufficiently neutralized so that it can be impregnated with acid-sensitive drugs such as thrombin.

EXAMPLE 2

Impregnation with Thrombin

A 3×4 inch piece of the neutralized cloth of Example 1 weighing 2.5 grams was added to 10 ml of distilled water containing 10,000 units of thrombin. The cloth was allowed to imbibe the thrombin solution and then was cut in 2×4 cm. pieces and tested for hemostatic efficacy using a swine splenic incision model. The neutralized cloth with the thrombin stopped bleeding in an average of 1 minute when tested on 6 wounds compared to unneutralized cloth dipped into a similar thrombin solution which stopped bleeding in the same test in an average of 6 minutes showing that the neutralized cloth can maintain the potency of the thrombin.

EXAMPLE 3

This is an example of the neutralization of an oxidized cellulose fabric in a mixture of methanol and water with sodium acetate as the neutralizing agent and the impregnation of the neutralized cloth with thrombin to make a dry, patient ready thrombin impregnated absorbable hemostat.

Two hundred and seventeen grams of an oxidized cellulose cloth with a carboxylic acid content of 15.2% were wrapped around a perforated core and then placed in a circulating bath equipped with a pump to circulate the solution up the core and through the cloth wrapped around it. The bath was filled with a mixture of 3 liters of methanol and 2 liters of water. Into the bath were placed 99.3 grams sodium acetate trihydrate. This weight of sodium acetate is the molar equivalent of the carboxylic acid on the oxidized cellulose, i.e. $217 \times 15.2\% = 32.9$ grams of carboxylic acid; $32.9/45 = 0.73$ moles of carboxylic acid; $(0.73 \times 136.1 = 99.3$ grams of sodium acetate trihydrate.

The sodium acetate dissolved in the aqueous methanol solution and this solution was circulated around the core for 30 minutes, after which time the pH of the solution stabilized at 5.3. The pH was raised to 5.4 by the addition of dilute sodium hydroxide to the circulating solution. The addition of sodium hydroxide to the solution can be done at this time, because the solution contains a buffer of sodium acetate and acetic acid, which moderates changes in the pH. If the buffer were not present, the addition of sodium hydroxide would result in a rapid rise in the pH and extensive swelling and weakening of the cloth. After the sodium hydroxide was added and the pH raised to 5.4 in the circulating bath, the cloth was removed from the circulating solution and washed with 2 liters of methanol for 10 minutes to remove water and salts from the cloth. This was repeated with another 2 liters of fresh methanol and then the cloth was air dried. The cloth was white, strong, and exhibited a pH in distilled water of 6.8. When titrated for carboxylic acid content, the neutralized cloth had a carboxylic acid content of 3.5%. Since the original cloth had a carboxylic content of 15.2%, the degree of neutralization was 76.9%.

A 3×4 inch (7.6 cm×10.2 cm) piece of this neutralized cloth was placed in a tray containing 5,000 units of thrombin dissolved in 10 ml of distilled water. The cloth was allowed to imbibe the thrombin solution. The saturated cloth was placed in a fresh tray, then placed on a cold shelf of a freeze dryer and allowed to freeze at $-20°$ C. When fully frozen the cloth was freeze dried by turning on the vacuum and was lyophilized for 16 hours. A portion of the freeze-dried cloth was assayed for thrombin the next day and found to contain 350 units per square inch (54.3 units/cm$^2$) of cloth. The cloth was packaged in foil, heat sealed and placed in a refrigerator for 1.5 years. After 1.5 years the thrombin-impregnated neutralized oxidized cloth was removed from the refrigerator and found still to be white and strong and to contain 280 units of thrombin per sq. in. (43.4 units/cm$^2$) of cloth; i.e., 80% of the remaining thrombin was viable. This patient-ready, thrombin-impregnated, absorbable hemostat was tested for hemostasis time using the swine splenic incision model and was found to stop bleeding on this model in an average of one minute when tested on six wounds, compared with 6.2 minutes for the untreated, non-thrombin impregnated oxidized cellulose starting material. This demonstrates that a dry, patient ready, neutralized and stable thrombin impregnated absorbable oxidized cellulose cloth can be prepared by the methods described in this example.

EXAMPLE 4

This is an example of the neutralization of oxidized cellulose cloth with dipotassium hydrogen phosphate in 4 parts water, 1 part methyl alcohol.

A quantity of 119.5 grams of oxidized cellulose cloth, with a carboxylic acid content of 18% (0.47 moles of carboxylic acid), was wrapped around a perforated core and placed in a reactor with a circulating pump. To the reactor was added 3.5 liters of water and 1.0 liter of methyl alcohol, and this was circulated around the core. A quantity of 81.8 grams of dipotassium hydrogen phosphate (0.47 moles) was dissolved in 500 ml of water and added to the circulating solution slowly at a rate of 10 ml/min. After 1 hour the pH of the circulating solution was 6.1 and showed no further change. The neutralized cloth was removed from the reactor and washed 3 times with 600 ml of methanol, then air dried. The cloth was white and exhibited a pH of 6.8 in purified water.

EXAMPLE 5

This is an example of the neutralization of oxidized cellulose cloth in 50:50, methanol:water using sodium acetate as the neutralizing agent and the use of the neutralized cloth as a hemostat.

A quanitity of 92.6 grams of an oxidized cellulose fabric with a carboxylic acid content of 18 weight percent (0.37 moles of acid) was wrapped around a core and placed in a reactor containing a mixture of 2.5 liters of water and 2.5 liters of methyl alcohol. To this solution were added 30.3 grams of anhydrous sodium acetate (0.37 moles). The solution was circulated for 1 hour. After this time the pH of the solution was 5.3 and remained constant. The cloth was removed, washed three times with 400 ml of methyl alcohol, and hung to air dry. The pH of the dry cloth in purified water was 5.76.

This neutralized cloth was sterilized by cobalt irradiation and tested on the swine splenic incision model for its hemostatic efficacy against the unneutralized cloth. The neutralized cloth stopped bleeding in an average of 3.1 minutes compared with the unneutralized cloth of 6.5 minutes when tested on 6 wounds. Thus hemostasis is achieved more rapidly with the neutralized cloth than with the unneutralized oxidized cellulose cloth.

EXAMPLE 6

This is an example of the impregnation of the neutralized cloth with fibrinogen and its use as a hemostat.

A 2×4 cm dry piece of neutralized oxidized cellulose weighing 80 mg with a pH greater than 5 as made by any of the previous examples is dipped into a solution containing 50 mg of fibrinogen per ml. The cloth imbibes 317 mg of this solution or about 15.8 mg of fibrinogen protein. The cloth is placed on a swine splenic incision of 1 cm in length and 1 mm in depth and is sprayed with one ml of thrombin solution containing 1,000 units of thrombin per ml. A fibrin clot develops almost immediately and bleeding is arrested within 30 seconds. This experiment is repeated on a total of 6 wounds and bleeding is stopped in an average of 30 seconds. When the experiment is carried out with fibrinogen impregnated non-neutralized cloth, bleeding is arrested in 3 minutes. This experiment demonstrates that the neutralized oxidized cellulose cloth can be impregnated with acid-sensitive fibrinogen and exhibits enhanced hemostatic activity over similarly impregnated non-neutralized cloth.

A number of examples demonstrate the use of neutralized oxidized cellulose—specifically neutralized INTERCEED* Barrier (N-INTERCEED) Barrier—for preventing post operative adhesions. These examples describe animal experiments that demonstrate the efficacy of treatments using N-INTERCEED Barrier impregnated with acid-sensitive anti-adhesion agents compared with non-neutralized oxidized regenerated cellulose barrier impregnated with such agents. It is also demonstrated in the cardiac model that the agent is as active with the delivery system as it is alone at optimum doses. Improved efficacy is shown for N-INTERCEED Barrier over existing non-neutralized oxidized cellulose barriers.

In vitro experiments demonstrate stability of anticoagulant drugs in the neutralized materials, contrasting them with instability of these drugs in the acid material. This serves as a model for preparation of impregnated patient-ready product.

TREATMENT OF N-INTERCEED BARRIER TO IMPROVE WETTABILITY

Neutralized oxidized cellulose may be treated with qlycerol to improve wettability, thus facilitating its ability to be impregnated with a medicament. An example of such a procedure is as follows:

A 125 g amount of N-INTERCEED Barrier was soaked for 20 minutes in 500 ml of a solution of 4% glycerol in isopropyl alcohol. The cloth was removed from the solution and allowed to air dry on paper towels for 2 to 3 hours.

Squares of glycerol-treated and non-glycerol-treated N-INTERCEED Barrier, 1.5 cm×1.5 cm, were placed in a petri dish, a drop of saline added to each one, and the pieces were observed. The glycerol-treated samples absorbed the saline more rapidly than the non-glycerol-treated N-INTERCEED Barrier samples.

ANIMAL MODELS

All animal surgical procedures were carried out according to the principles set forth in the "Guide for the Care and Use of Laboratory Animals" (Institute of Laboratory Animal Resources, National Research Council).

Uterine horn model

The model is as described by Linsky, C. B. et al. Adhesion reduction in the rabbit uterine horn model using an absorbable barrier, TC7, J. Reprod. Med., 32, (1), 1987, and in U.S. Pat. No. 4,840,626, issued Jun. 20, 1989. New Zealand female white rabbits weighing between 2.0 and 3.5 kg were acclimated in a vivarium for at least two weeks prior to use. Rabbits were individually housed in stainless steel cages. They were fed purina* Lab rabbit chow (Ralston purina Co., St. Louis) and given water ad libitum. Animals were fasted overnight prior to surgery. Anesthesia was induced by an intramuscular injection of 1 ml of a ketamine (Ketaset*)xylazine (Rompun*) solution [1 ml xylazine (20 mg/ml), 2 ml ketamine (100 mg/ml) and 1 ml sterile water). Additional anesthesia was administered via the marginal ear vein to maintain the animal on a surgical plane.

All animal surgery was done under aseptic conditions; this included an iodine scrub, draping, and use of sterile technique. Laparotomy was made through a lower midline incision and uterine horns are exposed. Five cm lengths of uterine horn starting 1 cm from the bifurcation were scraped using a #10 scalpel blade. The scrape, controlled in nature, fully removed the serosa and was characterized by engorgement of blood vessels and a small amount of punctate bleeding. Normally 20 strokes with the scalpel were sufficient to induce the described injury. In this model, hemostasis was achieved, when necessary, with tamponade. The animals were treated by covering each horn with enough fabric so as to completely cover the injured area, i.e., the fabric was cut to a piece 2 inches by 3 inches (5 cm×7.6 cm). The appropriate dosage of drug was then applied to the area by moistening the fabric with 1 ml of the drug solution. The horns of control animals were left untreated, i.e., no fabric or drug is used.

The musculo-peritoneal layer was closed with 4-0 Vicryl* suture (Ethicon, Somerville, NJ), the cutaneous layer with skin staples. Animals were evaluated for adhesions two weeks after surgery. Evaluation was done via scoring which considered both the extent and severity of the adhesions. The scoring system relies on the fact that an extensive length of uterine horn is traumatized; thus extent of adhesions can be quantified by measuring the length of the horn to give the following grading:

0 = No adhesions
1 = 25% of traumatized area
2 = 50% of traumatized area
3 = Total involvement Fractional scores were given for extent of adhesions intermediate between the above grades. The severity (tenacity) of the adhesions was measured as follows:
0 = No resistance to separation
0.5 = Some resistance (moderate force required)
1 = Sharp dissection needed The total grade thus is additive giving a range of adhesion scores of 0-4, which represent both extent and severity. Thus a score of 0 represents no adhesions while a score of 4 represents the most severe extent and severity of adhesions.

In addition to analyses of scores on some experiments, actual measurements of test segment of uterine horn lengths involved in adhesions were analyzed. These data permit parametric statistical analysis. Furthermore, these analyses permit greater discrimination among treatment groups when uterine horns have involvement in adhesions greater than 50%. A value of 0 represents no adhesions and 5 cm represents total involvement of the test segment of uterine horn.

Modified Uterine Horn Model: (Bleeding Surgical Site)

The uterine horn model was modified to test the efficacy of adhesion barriers at a bleeding surgical site, providing a more severe challenge. The procedure for the uterine horn model was performed as described above. In addition to scraping the uterine horns in the standard manner, further bleeding was initiated by nicking four small blood vessels on each uterine ligament. Hemostasis was not achieved subsequent to this procedure.

Cardiac Model:

White New Zealand rabbits of either sex (3.0-4.0 kg) were housed individually and fed purina Lab Rabbit Chow HF 5326 (purina Company, St. Louis, Mo.). All animals were acclimated in the vivarium for at least two weeks prior to use. They were given food and water ad libitum but solid food was withheld for one night prior to surgery.

Animals were weighed. Anesthesia was induced using intravenous ketamine (50 mg/ml)/xylazine (5 mg/ml) and maintained following endotracheal intubation with methoxyflurane (0.5-3%, in oxygen) by inhalation. The thoracic skin was shaved using electric clippers and swabbed with 70% ethanol and then povidone iodine solution. Sterile drapes were applied and surgery performed using aseptic technique.

The thorax was opened via a median sternotomy; bleeding was controlled using electrocautery. Any blood clots remaining on or around the pericardium were removed prior to opening the pericardium medially. The thorax of the rabbit was entered via a midline sternal incision. Hemostasis of the sternal incision was achieved by electrocautery. The pericardium was opened and the anterior surface of the heart was abraded by stroking forty times with a gauze-wrapped forefinger. An elliptical piece of oxidized regenerated cellulose fabric with axes 2"×3" (5 cm×7.6 cm) was draped over the anterior surface of the heart and around the apex to the posterior surface. The acid-sensitive active agent was delivered to the oxidized regenerated cellulose fabric and was absorbed by it. The thorax was closed in layers. The animal was sacrificed four weeks after surgery and the anterior surface of the heart and the underside of the sternum evaluated for adhesions. The percentage adhesion involvement of a strip 1 cm wide and extending from the apex to the base of the anterior cardiac surface was estimated. Thus, a score of 100% represents the greatest extent of adhesions and 0% represents no adhesions. This strip represents the surface of the heart in intimate contact with the sternum, where adhesions are most likely to occur and cause a problem for the surgeon attempting a reentry to the thorax.

EXAMPLE 7

Neutralized INTERCEED Barrier preserves activity of rapidly acid-labile agents: t-PAA In this example, t-PAA is tissue plasminogen activator analogue (Fb-Fb-CF) (Creative BioMolecules, Hopkinton, Mass.) and consists of a single chain of two fragments B of protein A from *Staphylococcus aureus* and the catalytic fragment of t-PA. The fibrinolytic activity of Fb-Fb-CF is determined by a chromogenic assay using S-2251 as the substrate. The specific activity of Fb-Fb-CF is estimated to be $5 \times 10^5$ iu/mg protein in reference to the International Standard for t-PA. It is produced by recombinant DNA technology by expression in and extraction from *Escherichia coli* (See Crea, R. et al, Protein analogues of tissue plasminogen activator. International Patent application W087/05934, 1987; Phillips, D.A. et al., The effects of a new tissue plasminogen activator analogue, Fb-Fb-CF, on cerebral reperfusion in a rabbit embolic stroke model. Ann. Neurol. 25:281, 1989 )

This experimental series, using the uterine horn model, demonstrates that t-PAA delivered on N-INTERCEED Barrier reduces the adhesion score below that of INTERCEED Barrier, N-INTERCEED Barrier, and t-PAA delivered on INTERCEED Barrier.

| Uterine horn model: | | |
|---|---|---|
| Treatment | No Horns | Adhesion Score |
| Control | 6 | 4.00 |
| INTERCEED Barrier + 1.25 mg t-PAA | 12 | 3.62 |
| INTERCEED BARRIER + 0.125 mg t-PAA | 10 | 1.56 |
| Control | 12 | 3.50 |
| INTERCEED Barrier + saline | 12 | 2.06 |
| N-INTERCEED Barrier + tris buffer** | 12 | 1.81 |
| N-INTERCEED Barrier + 1.25 mg t-PAA | 12 | 0.79 |
| N-INTERCEED Barrier + 0.125 mg t-PAA | 12 | 1.08 |

**Tris buffer was used as control solution for t-PAA, because the manufacturer prepared the product in this buffer (5 mm Tris. HCl, 2 mm EDTA). The pH of a 2" × 3" (5 cm × 7.6 cm) piece of N-INTERCEED Barrier in 2 ml Tris buffer is 4.8, but in saline is 3.9. The lower limit of pH to preserve activity of t-PAA is 4 (manufacturer information). The pH of the peritoneal fluid of rabbits is 7.5 to 8. The pH of the peritoneal fluid of humans is 6.8–9.8 (Biology Data Book, Second Ed, Vol III, Ed Altman P. E., Ditmer, D. S., Federation of American Society for Experimental Biology, 1974).

The following cardiac adhesion model experiment supports the concept that the N-INTERCEED Barrier matrix does not interfere with the activity of t-PAA.

| Cardiac model: | | |
|---|---|---|
| Treatment | No | % Central Area w/Adhes |
| Control | 8 | 86.2 |
| N-INTERCEED Barrier + buffer | 7 | 88.6 |
| N-INTERCEED Barrier + t-PAA 0.94 mg | 6 | 23.2 |
| t-PAA 0.94 mg alone | 5 | 28.0 |
| Control | 7 | 85.7 |
| N-INTERCEED Barrier + t-PAA 0.94 mg | 8 | 16.3 |

EXAMPLE 8

Neutralized INTERCEED Barrier preserves the activity of rapidly acid-labile agents: t-PA

| Cardiac model: | | |
|---|---|---|
| Treatment | No | % Central Area w/Adhes |
| Control | 4 | 97.5 |
| N-INTERCEED Barrier | 6 | 64.2 |
| N-INTERCEED Barrier + 0.94 mg t-PA | 4 | 3.8 |
| 0.94 mg t-PA | 2 | 0.0 |
| N-INTERCEED Barrier + 0.19 mg t-PA | 5 | 90.0 |
| 0.19 mg t-PA | 2 | 0.0 |

It is noted that the N-INTERCEED Barrier interferes with the activity of the t-PA at low dose levels.

EXAMPLE 9

Neutralized SURGICEL Hemostat preserves the activity of rapidly acid-labile agents: Streptokinase.

| Uterine horn model: | | |
|---|---|---|
| Treatment | No Horns | Adhesion Score |
| Control | 12 | 3.38 |
| N-SURGICEL + 125000 IU streptokinase | 12 | 1.88 |
| N-SURGICEL | 12 | 2.83 |

EXAMPLE 10

Neutralized INTERCEED Barrier preserves the activity of rapidly acid-labile agent: Streptokinase

| Cardiac model: | | |
|---|---|---|
| Treatment | No | % Central Area w Adhes |
| Control | 3 | 93.3 |
| N-INTERCEED + 93750 IU streptokinase | 7 | 32.9 |
| 93750 IU streptokinase | 7 | 48.6 |

EXAMPLE 11

Neutralized oxidized cellulose product preserves activity of slowly acid-labile agent: stable heparin-impregnated product.

Methods

The material is impregnated with a solution of the adhesion-preventing material, air dried, sealed in moisture-proof foil pouches, and sterilized by cobalt irradiation. The biological activity is measured by eluting the impregnated fabric in 0.90% sodium chloride and testing the eluted solution by Activated Partial Thromboplastin Time Test (APTT) (Thrombofax, Ortho Diagnostic Systems).

INTERCEED Barrier was impregnated with 1667 units of heparin sodium per 3"×4" (7.6 cm×10.2 cm) piece. Potency of the commercial heparin sodium used in these experiments in USP units was determined by the manufacturer in accordance with the regulations defined by The United States Pharmacopeia XXII, 1990, p 633. Samples were stored at room temperature (approximately 26° C.). Heparin activity was determined 0,1,7,14, and 28 days later. Results demonstrate that the heparin is inactivated over time.

| Heparin Activity by APTT Test-Impregnated INTERCEED Barrier | | |
|---|---|---|
| Days post sterilization | No. Tested | % of orig. activity |
| 0 | 3 | 85 |
| 1 | 3 | 77 |
| 7 | 3 | 58 |
| 14 | 3 | 47 |
| 28 | 3 | 30 |

Neutralized SURGICEL * Absorbable Hemostat (N-SURGICEL Hemostat) was impregnated with 2000 units of heparin per 3"×4" (7.6 cm×10.2 cm) piece. SURGICEL Hemostat used as the oxidized cellulose in this experiment had been neutralized in the same manner as was INTERCEED Barrier. Samples were stored at 4° and 30° C. Heparin activity was determined 0, 1, 6, 14, 30 and 60 days subsequently. Results show that heparin is not inactivated over time.

| Heparin Activity by APTT Test-Impregnated N-SURGICEL Hemostat | | | |
|---|---|---|---|
| | No tested | % of orig. activity | |
| Days post sterilization | per temp | 4° C. | 30° C. |
| 0 | 3 | | 108 |
| 1 | 3 | | 98 |
| 6 | 3 | 95 | 91 |
| 14 | 3 | 96 | 93 |
| 30 | 3 | 89 | 90 |

-continued

Heparin Activity by APTT Test-Impregnated N-SURGICEL Hemostat

| Days post sterilization | No tested per temp | % of orig. activity 4° C. | 30° C. |
|---|---|---|---|
| 60 | 3 | 95 | 93 |

N-INTERCEED Barrier was impregnated with 2000 units of heparin per 3"×4" piece. Heparin activity was determined 0, 1 and 77 days subsequently. Results demonstrate that the heparin is not inactivated over time.

Heparin activity by APTT Test-Impregnated N-INTERCEED Barrier

| Days post sterilization | No tested | % of original activity |
|---|---|---|
| 1 | 3 | 98.2 |
| 77 | 2 | 94.0 |

EXAMPLE 12

N-INTERCEED Barrier preserves the activity of a slowly acid labile low molecular weight heparin, FRAGMIN*: stable low molecular weight heparin-impregnated product.

IMPREGNATION OF N-INTERCEED BARRIER

When N-INTERCEED Barrier is impregnated with an aqueous solution of a medicament, the fibers begin to swell and become distorted. If this neutralized cloth is air dried, some decomposition of the cloth takes place during the drying process, producing yellow chromophoric breakdown products. If the cloth is freeze-dried, then the decomposition is minimized. If the cloth is impregnated with a solution of a medicament in alcohol, the swelling and decomposition of the cloth is supressed, and a whiter cloth is produced upon air drying from the alcohol solution. A 50% or 60% ethanol in water solution of a drug can be used to impregnate N-INTERCEED Barrier. The material is air dried, dehumidified under vacuum without heat, sealed in moisture-proof foil pouches and sterilized by cobalt 60 irradiation. Pieces of N-INTERCEED Barrier 3"×4" were impregnated with 2 ml/piece of an alcoholic solution containing either 100 or 125 anti-$X_a$ units of FRAGMIN*/ml, air dried, dehumidified under vacuum without heat, sealed in moistureproof foil pouches and sterilized by cobalt 60 irradiation. Observations after at least two months aging at 30° C. were as follows:

| % ethanol | | | | |
|---|---|---|---|---|
| 0 | 30 | 40 | 50 | 60 |
| streaked | streaked | streaked | not streaked | not streaked |
| brittle | not brittle | not brittle | not brittle | not brittle |

N-INTERCEED and INTERCEED were impregnated with FRAGMIN (KabiVitrum AB, Stockholm, Sweden), a low molecular weight heparin, 100 anti-$X_a$ units per 3"×4" piece. Potency of FRAGMIN is measured by its ability to inhibit the coagulation protease, Activated Factor X in Anti-Factor $X_a$ units by a method chosen by the manufacturer. An example of an Anti-Factor $X_a$ assay method is found in the United States Pharmacopeia XXII, 1990 p. 633 Official Monograph for Heparin Sodium. Measures of biological activity may also be taken by Activated Partial Thromboplastin Time test (APTT).

Biological activity was determined one and two months after preparation by APTT test. Results show that the impregnated INTERCEED loses 70% of its FRAGMIN activity in one month, but heimpregnated N-INTERCEED retains all of its activity through 60 days.

FRAGMIN activity by APTT test-impregnated N-INTERCEED/INTERCEED

| Impregnated material | days post sterilization | number tested | % of original activity |
|---|---|---|---|
| INTERCEED | 30 | 4 | 37.9 |
| N-INTERCEED | 30 | 4 | 100.8 |
| INTERCEED | 60 | 3 | 29.0 |
| N-INTERCEED | 60 | 4 | 105.3 |

EXAMPLE 13

N-INTERCEED Barrier provides greater efficacy in adhesion prevention than INTERCEED Barrier

| | Cardiac model: | | |
|---|---|---|---|
| Treatment | No. of Animals | % Central Area w/Adhes. | SEM |
| Control | 15 | 84 | 6.7 |
| INTERCEED Barrier + saline | 7 | 89 | 8.6[1] |
| N-INTERCEED Barrier + saline | 15 | 41 | 10.3[2,3] |

Comparisons made with Student's t-test:
1. INTERCEED vs control, 2P=0.7
2. N-INTERCEED vs control, 2P=0.002
3. N-INTERCEED vs INTERCEED, 2P=0.009

Uterine horn model:

Uterine horn scores from 13 experiments were pooled. The frequency of scores in each treatment group were recorded as follows;

Scores from a total of 284 horns (142 rabbits) are analyzed here.

| | Distribution of Horns by Adhesion Scores | | |
|---|---|---|---|
| Score | Control | INTERCEED | N-INTERCEED |
| 0.0 | 9 | 13 | 39 |
| 0.2 | 2 | | |
| 0.4 | | | 1 |
| 0.5 | | 3 | |
| 0.8 | | 3 | 2 |
| 1.0 | 1 | 12 | 2 |
| 1.5 | 3 | 15 | 6 |
| 2.0 | 3 | 8 | |
| 2.5 | 4 | 5 | 7 |
| 3.0 | 10 | 23 | 2 |
| 3.5 | 7 | 1 | 5 |
| 4.0 | 75 | 19 | 4 |
| N | 114 | 102 | 68 |

Comparison of adhesion scores using Wilcoxon Rank-sum test: N-INTERCEED Barrier performed significantly better than INTERCEED Barrier, 2P<0.001.

Comparison of Treatment Groups by Horn Length Involved with Adhesions

| Treatment | No Horns | Horn Length With Adh (cm) | SD (N-1) |
|---|---|---|---|
| Control | 99 | 3.37 | 1.782 |
| INTERCEED + Saline | 102 | 1.46 | 1.381 |
| N-INTERCEED + Saline | 68 | 0.87 | 1.412 |

Comparison of horn length involved with adhesion using Student's t-test:
N-INTERCEED Barrier performed significantly better than INTERCEED Barrier, 2P=0.008.

EXAMPLE 14

N-INTERCEED Barrier provides greater efficacy in adhesion prevention than INTERCEED Barrier at a bleeding surgical site.

Modified uterine horn model (Bleeding surgical site):
Analyses of horn lengths involved in adhesions of three studies show a significant difference between controls and treatment with N-INTERCEED Barrier. No difference was found between controls and treatment with INTERCEED Barrier.

| Treatment | No | Adh Score | Length of Horn w/Adh (cm) | SD |
|---|---|---|---|---|
| Study | | | | |
| Control | 12 | 4.00 | 4.54 | 0.69[1] |
| N-INTERCEED | 12 | 2.21 | 1.79 | 1.51[1] |
| Two Studies | | | | |
| Control | 24 | 3.71 | 4.16 | 1.32[2] |
| INTERCEED | 26 | 3.42 | 3.71 | 1.63[2] |

Comparisons made with Student3 s t-test:
1. N-INTERCEED vs control 2P<0.001
2. INTERCEED vs control, NS, 2P>0.05

The scope of the present invention is not limited by the description, examples and suggested uses herein, and modifications can be made without departing from the spirit of the invention. For example, the thrombin-impregnated neutralized oxidized cellulosic material may be used in first aid treatment of wounds. Other ingredients; for example, antiseptic additives such as silver salts, may also be added to the material.

Application of the compositions and methods of the present invention for medical and surgical uses can be accomplished by any suitable surgical and medical method and technique that is presently, or may be prospectively, known to those skilled in the art. Thus, it is intended that the present invention cover the modifications and variations of this invention that come within the scope of the appended claims and their equivalents.

What is claimed is:

1. A process for preparing a storage stable, non-irritating and therapeutic neutralized oxidized cellulose product comprising the steps of:
contacting an acidic oxidized cellulose material with an alcohol and water solution of a slightly basic chloride-free salt of a weak acid selected from the group consisting of sodium acetate, potassium acetate, sodium citrate, sodium formate, potassium citrate, potassium formate, disodium hydrogen phosphate, dipotassium hydrogen phosphate, and mixtures thereof to elevate the pH of said cellulose material to between 5 and 8;
washing the elevated pH cellulose material with alcohol to remove excess salt and water therefrom; and
drying the cellulose material to remove alcohol.

2. The process of claim 1 wherein the alcohol and water solution has a ratio of from 4:1 to about 1:4 of alcohol to water.

3. The process of claim 1 wherein the alcohol of the water and alcohol solution is methanol in a ratio of from 3:2 to 1:1 methanol to water.

4. The process of claim 1 wherein the slightly basic salt of a weak acid is sodium acetate.

5. The process of claim 4 wherein the amount of sodium acetate used is about equal to that of the carboxylic acid present on the oxidized cellulose material, on a molar basis.

6. The process of claim 4 wherein the alcohol and water solution is from about 3:2 to about 1:1 methanol to water.

7. The process of claim 1 including the additional step of impregnating the dried material with a hemostatic effective amount of thrombin.

8. The process of claim 7 wherein 3.5 to 9.0 units of thrombin is applied per milligram of cellulose material.

9. The process of claim 1 including the additional step of applying glycerol to the dried material to improve its wettability.

10. The process of claim 9 including the additional step of impregnating the dried material with an acid-sensitive medicament, biologic or enzyme.

11. The process of claim 10 wherein the acid-sensitive medicament, biologic or enzyme is selected from the group consisting of plasma proteins, wound healing proteins, glycosaminoglycans and antifibrinolytics.

12. The process of claim 11 wherein the plasma protein is fibrinogen, the wound healing protein is an epidermal derived growth factor, the glycosaminoglycan is hyaluronic acid and the antifibrinolytic is Aprotinin.

13. The storage stable product produced by the process of claim 1.

14. The storage stable product produced by the process of claim 10.

15. A mammalian hemostatic method comprising the step of applying the storage stable product of claim 13 to a hemorrhaging site of a mammal.

16. A mammalian hemostatic method comprising the step of applying the storage stable thrombin-containing product produced by the process of claim 7 to a hemorrhaging site of a mammal.

17. A mammalian therapeutic method comprising the step of therapeutically applying the storage stable product of claim 14 to a mammal.

18. The process of claim 9 including the additional step of impregnating the dried material with an acid-sensitive surgical adhesion-preventive substance.

19. The process of claim 18 in which the adhesion-preventive substance is selected from the group consisting of tissue plasminogen activator, tissue plasminogen activator analogue, streptokinase, heparin, low molecular weight heparin, and pentasaccharide.

20. A storage stable product produced by the process of claim 18.

21. A process for preventing surgical adhesions which comprises positioning as a physical barrier, between the site of the surgical activity and neighboring tissue, a product produced by the process of claim 1.

22. A process for preventing surgical adhesions which comprises positioning as a physical barrier, between the site of the surgical activity and neighboring tissue, a product produced by the process of claim 18.

* * * * *